United States Patent [19]

Ford

[11] 4,374,476
[45] Feb. 22, 1983

[54] VACUUM VAPORIZING METHOD AND APPARATUS

[75] Inventor: Gregory A. Ford, Bartlesville, Okla.

[73] Assignee: Phillips Petroleum Company, Bartlesville, Okla.

[21] Appl. No.: 855,489

[22] Filed: Nov. 28, 1977

[51] Int. Cl.³ .......................................... G01N 31/08
[52] U.S. Cl. ................................................. 73/23.1
[58] Field of Search ............ 73/23.1, 23, 19, 422 GC; 23/232 C, 254; 219/201, 271, 279

[56] References Cited

U.S. PATENT DOCUMENTS

| | | | |
|---|---|---|---|
| 3,069,894 | 12/1962 | Claudy | 73/23.1 |
| 3,119,004 | 1/1964 | Hoop | 219/200 |
| 3,236,092 | 2/1966 | Carter | 73/23.1 |
| 3,368,385 | 2/1968 | Harvey | 73/23.1 |
| 3,372,573 | 3/1968 | Sanford | 73/23.1 |
| 3,483,754 | 12/1969 | Chambers | 73/422 GC |
| 3,673,853 | 7/1972 | Griswold et al. | 73/19 |
| 3,844,160 | 10/1974 | Yamaoka | 73/19 |
| 3,933,165 | 1/1976 | Budzak et al. | 73/422 GC |
| 4,067,226 | 1/1978 | Ririe | 73/23.1 |

OTHER PUBLICATIONS

Fisher et al., "Highly Sensitive Elec. Discharge Detector For Chrom. Analysis", *Analytical Chemistry*, pp. 1208-1210, Sep., 1965.

*Primary Examiner*—Stephen A. Kreitman

[57] ABSTRACT

A closed chamber with a variable volume is used as a vacuum vaporizer. The vacuum vaporizer can be used in a gas chromatographic apparatus. A method of analyzing hard-to-vaporize liquids is also given.

8 Claims, 4 Drawing Figures

VACUUM VAPORIZING METHOD AND APPARATUS

FIELD OF THE INVENTION

This invention relates to a new use of a closed chamber having a variable volume. In one aspect, it relates to a gas chromatographic apparatus constructed with the above-mentioned chamber. In another aspect, it relates to a method of analyzing hard-to-vaporize liquid samples with gas chromatography.

BACKGROUND OF THE INVENTION

How to construct a vacuum vaporizer having good seals is an important problem. The prior art has employed diaphragms to solve this problem.

To analyze a liquid with the methods of gas chromatography, the liquid must be first vaporized. Hard-to-vaporize liquids which break down upon being heated present special problems in gas chromatographic analyses.

An object of this invention is to provide an improved method of vacuum vaporizing.

A further object of this invention is to provide an improved gas chromatography analysis apparatus.

A still further object of this invention is to provide a method of analyzing hard-to-vaporize liquids with gas chromatography.

STATEMENT OF THE INVENTION

According to the invention, a sealable chamber one wall of which is a piston head is used as a vacuum vaporizer. Also, according to the invention, the chamber is used as a part of a gas chromatography analysis method for analyzing hard-to-vaporize liquids. And further, according to the invention, a gas chromatography analysis apparatus is provided.

PREFERRED EMBODIMENTS OF THE INVENTION

Figure 1:
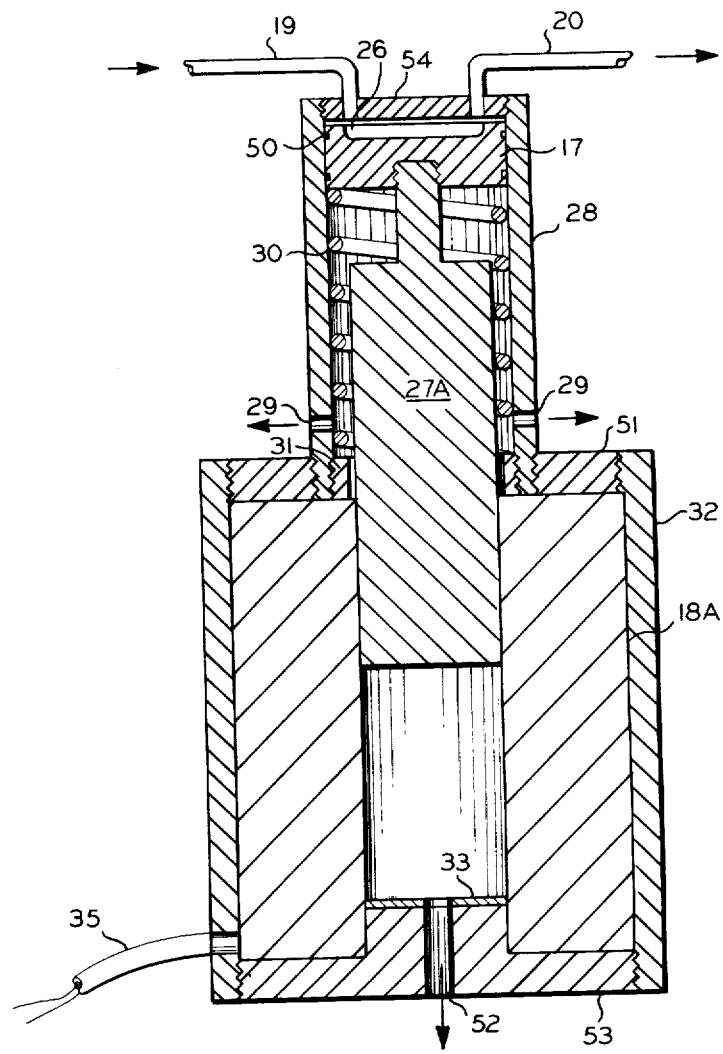
FIG. 1 is a diagrammatic illustration of an embodiment of a vacuum vaporizer according to the invention.

Referring to FIG. 1, piston 17 reciprocates within vacuum chamber 28. Sample liquid is introduced through intake port 19 into a hollowed out portion 26 of piston 17. When the current in solenoid coil 18A is switched on by timing mechanism 10 (shown in FIG. 3), plunger 27A is drawn inside solenoid coil 18A, pulling piston 17 down, increasing the volume into which the liquid sample vaporizes, and compressing spring 30 (which is supported by spring retainer 31, a part of case 32). Breather ports 29 and 52 allow air contained within the spaces below piston 17 and plunger 27A to escape. At its maximum displacement from its initial position, plunger 27A contacts teflon spacer 33. At that time, the current is switched off and spring 30 acts to force plunger 27A back to its starting position, thereby forcing the vaporized sample out of vacuum chamber 28 through exhaust port 20.

Figure 2:
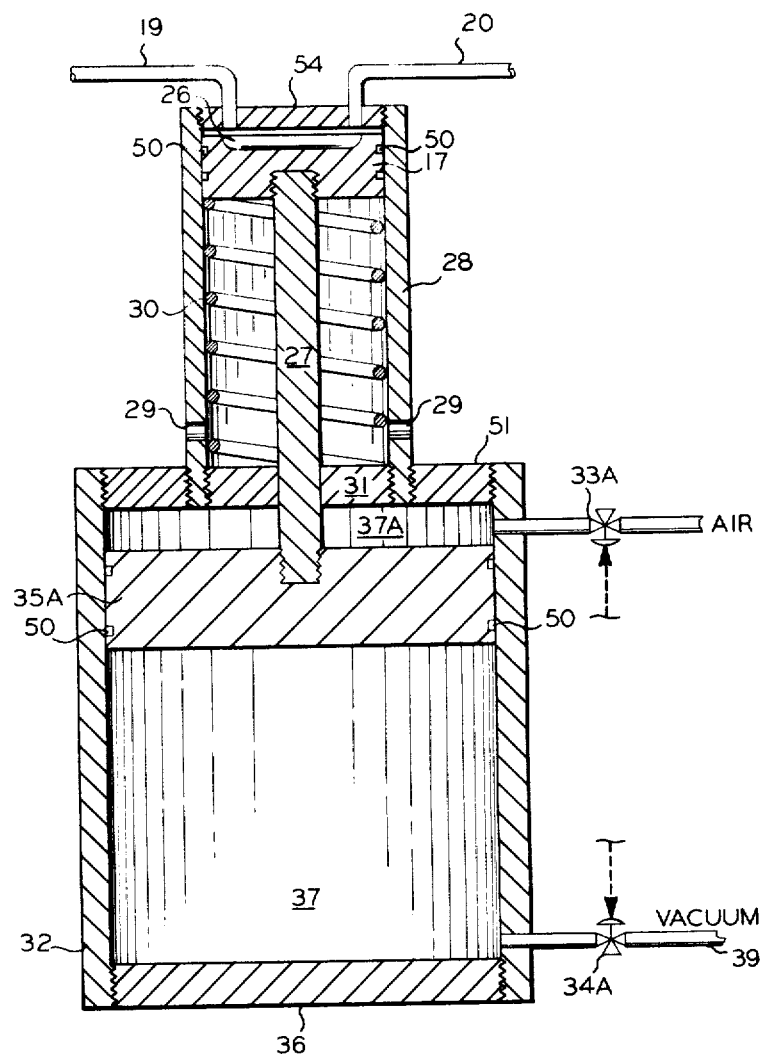
FIG. 2 is a diagrammatic illustration of another embodiment of a vacuum vaporizer according to the invention.

Various parts of the apparatus shown in FIGS. 1 and 2 preferably contain threads which facilitate their assembly. In FIG. 1 and in FIG. 2, intake port 19 and exhaust port 20 are screwed into top section 54 which with spring retainer 31 and section 51 are screwed onto vacuum chamber 28, which is itself then screwed into case 32. The bottom of case 32, which is threaded end cap 36 in FIG. 2 and threaded end cap 53 (containing breather port 52) in FIG. 1, also can be threaded into case 32. In FIG. 1, plunger 27A can be screwed into piston 17; and in FIG. 2, piston rod 27 can be screwed into both piston 17 and actuating piston 35A.

Figure 3:
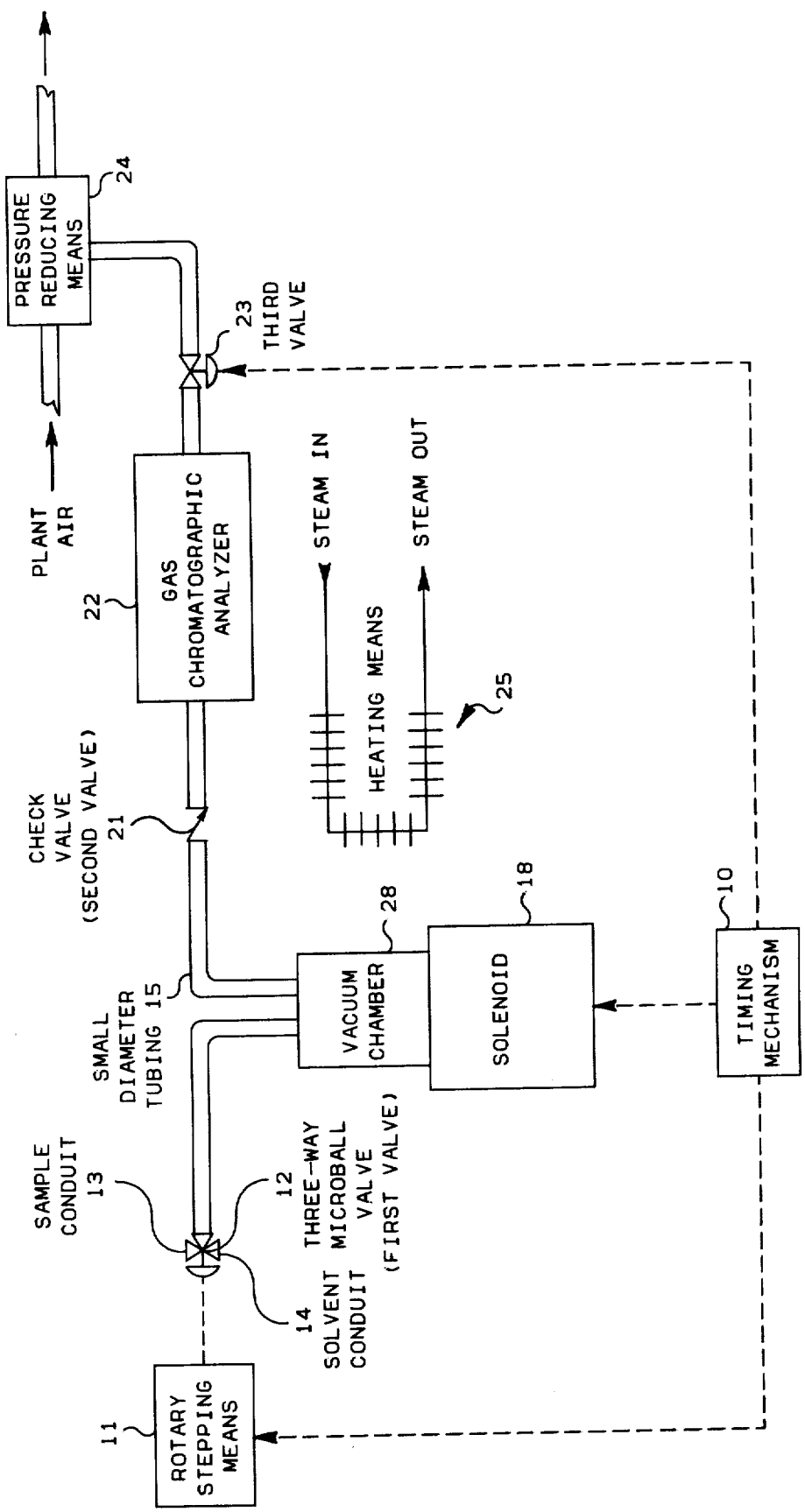
FIG. 3 is a diagrammatic illustration of gas chromatographic apparatus according to the invention.

In FIG. 1, coil terminal 35 connects solenoid coil 18A with timing mechanism 10 shown in FIG. 3.

In the embodiment of FIG. 2, both a pressurized gas and a vacuum source 39 are used to actuate piston 17. Sample liquid is introduced through intake port 19 into a hollowed out portion 26 of piston 17. Then, the pressurized gas, for example air, is introduced through 3-way valve 33A at the same time that vacuum 39 is applied to 3-way valve 34A, serving to force actuating piston 35A down to its maximum displacement from its initial closed position. Piston 17, which is rigidly connected to actuating piston 35A, is also forced down. Then, 3-way valves 33A and 34A both open to the atmosphere, allowing air to enter at valve 34A and allowing air to exit at valve 33A; simultaneously, the restoring force of spring 30, now compressed, acts to force piston 17 back to its uppermost position in the cycle. This operation of valves 33A and valves 34A can, for example, be accomplished by use of a rotary stepping means (not shown) connected to 3-way valve 33A and another rotary stepping means (not shown) connected to 3-way valve 34A. The rotary stepping means can be operated by timing mechanism 10, according to the timing diagram of FIG. 4B, wherein the ON position of solenoid 18 corresponds to the positions of the stepping means in which valve 33A is open to the gas under pressure and valve 34A is open to vacuum 39. The ON position of solenoid 18 also corresponds, therefore, to the application of pressure to actuating piston 35A. The OFF position of solenoid 18 in FIG. 4B corresponds to the positions of the stepping means in which valve 33A and valve 34A are both open to the atmosphere.

There are a variety of other methods of actuating reciprocating piston 35A, and all such possible methods are within the scope of this invention. For example, gas under pressure without a vacuum source can be used to actuate piston 35A; and it can, for example, be applied at valve 33A, while valve 34A is simply left continuously open to the atmosphere. The timing diagram of FIG. 4B can be employed (wherein the ON position of solenoid 18 corresponds to the position of the stepping means in which valve 33A is open to the gas under pressure and the OFF position of solenoid 18 corresponds to the position of the stepping means in which valve 33A is open to the atmosphere). Another example is to use a vacuum source 39 at valve 34A without applying a gas under pressure; then, valve 33A is left continuously open to the atmosphere. In that situation, the timing diagram of FIG. 4B can be employed (wherein the ON position of solenoid 18 corresponds to the position of the stepping means in which valve 34A is open to the vacuum and the OFF position of solenoid 18 corresponds to the position of the stepping means in which valve 34A is open to the atmosphere). In the above-described examples, a suitable spring for use is that used in FIG. 2, so that the restoring force of a compressed spring acts to push piston 17 up to its closed position.

Another alternative is to employ hydraulic pressure, introducing a liquid through valve 33A for example, while valve 34A is left continuously open to the atmosphere. Again, the timing diagram of FIG. 4B can be used, (wherein the ON position of solenoid 18 corresponds to the position of the stepping means in which valve 33A is open to the liquid under pressure and the OFF position of solenoid 18 corresponds to the position of the stepping means in which valve 33A is open to a receptacle for the liquid which has been used); and a suitable spring is that described for use with FIG. 2.

When air or other fluid is introduced or withdrawn from case 32, the orifices in case 32 must be large enough so that the fluid will quickly flow in or out.

Obviously, other spring arrangements can be employed. For example, a spring under tension can be placed in space 37A, connected to piston 35A and case 32, to provide the force needed to bring piston 17 back to its uppermost position in its cycle (after gas or liquid under pressure has been introduced through valve 33A to force actuating piston 35A down). Alternatively, a spring under compression can be placed in space 37 to accomplish this function.

Referring now to FIG. 3, timing mechanism 10 activates rotary stepping means 11, which in turn adjusts 3-way microball valve (first valve) 12 to permit a quantity of a liquid sample to enter vacuum chamber 28 through intake port 19, by way of sample conduit 13. This procedure takes place during the time interval ($t_1$-$t_0$) shown in FIG. 4A. Then, 3-way microball valve 12 returns to its original, closed position; and intake port 19 is sealed. Exhaust port 20 is sealed off by check valve 21. Timing mechanism 10 then activates solenoid coil 18A or, alternatively, valves 33A and/or 34A (shown in FIG. 2). Upon activation, piston 17 moves so as to cause the volume of vacuum chamber 28 to increase and thereby to cause the pressure in vacuum chamber 28 to decrease. This decrease in pressure acts to cause the liquid in vacuum chamber 28 to vaporize. For very hard-to-vaporize liquids, heating means 25 may also be used to aid in the vaporization.

When piston 17 is at the point in its cycle such that the volume of chamber 28 is at a maximum (that point is here called the open position of the piston), third valve 23 opens and the vapors of the sample are drawn by pressure reducing means 24 out of exhaust port 20, by way of small diameter tubing 15, through check valve (second valve) 21, and into analyzer 22. This operation of pressure reducing means 24 also serves to aid piston 17 to return to its closed position, as does the restoring force of spring 30. Third valve 23 remains open during the analysis of the sample. After analysis is completed, the vapors are drawn out of the system. Timing mechanism 10 then closes third valve 23. Next, a quantity of a solvent is introduced into the system for cleaning via solvent conduit 14. The cycle described above is then repeated, except that the analysis step is omitted.

Figure 4:
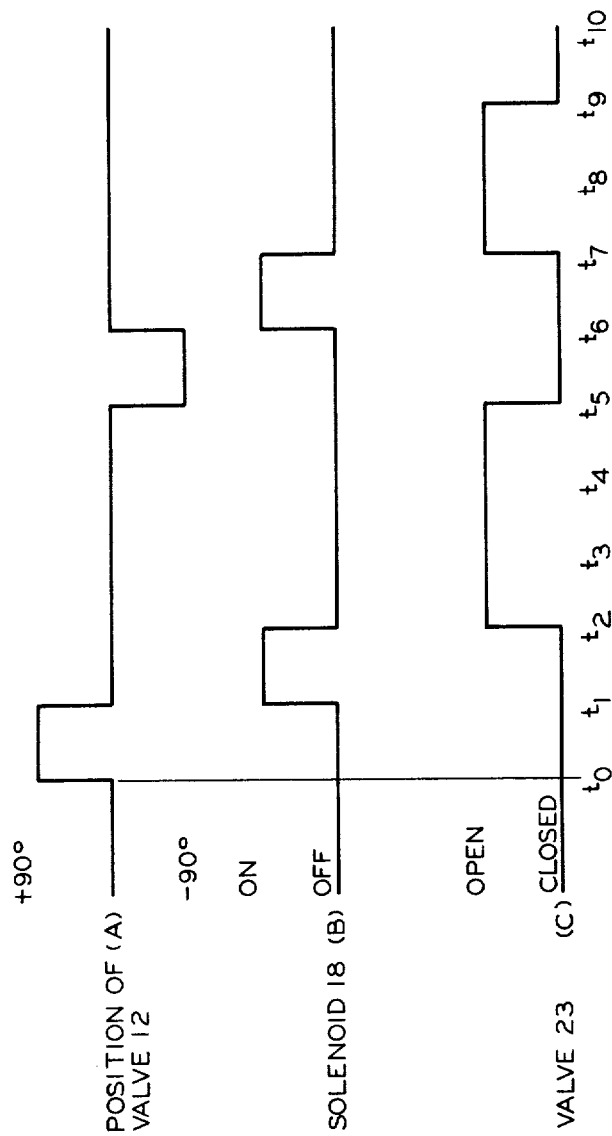
FIG. 4 is a timing diagram of the operation of the system shown in FIG. 3.

FIG. 4 is a suitable timing diagram for the operation just described. FIG. 4A is a plot of the 3 positions of 3-way microball valve 12 (of FIG. 3) as a function of time. From time $t_0$ to time $t_1$, the valve is open to allow sample into the system. Then the valve closes and remains closed, acting to seal intake port 19 until time $t_5$, when solvent is introduced into the system. At time $t_6$ the valve then returns to the closed position. FIG. 4B shows the times when actuating solenoid 18 is switched on (or, alternatively, when pneumatic or hydraulic pressure is applied) after the sample or solvent has been introduced into chamber 28. FIG. 4C is a plot of the open and closed positions of third valve 23 as a function of time. After the sample has been vaporized in chamber 28, at time $t_2$, third valve 23 opens and remains open while the sample is removed from chamber 28 (from $t_2$ to $t_3$), while the sample is in the analyzer (from $t_3$ to $t_4$), and while the sample is being exhausted from the system (from $t_4$ to $t_5$). Then third valve 23 closes and remains closed until the cleaning solvent vapor is to be removed from the vacuum chamber (from $t_7$ to $t_8$) and exhausted from the system (from $t_8$ to $t_9$).

Piston 17 is shaped to fit snugly within vacuum chamber 28 yet to be able to move freely through its cycle.

Piston 17 (shown in FIGS. 1 and 2) and actuating piston 35A (shown in FIG. 2) are fitted with piston sealing rings 50, which are well known in the art. The rings should be chosen so that a minimum of leakage results, so that a vacuum can be achieved, and so that the pistons are able to move freely through their respective cycles.

The heating means 25 (shown in FIG. 3) for the vacuum chamber 28 is preferably located outside the chamber so as not to interfere with the movement of the piston. The heating means 25 can be any suitable heating means such as steam tracing, for example, the only requirement being that heating be adjustable so that the sample liquids and vapors do not reach their decomposition temperatures. Heating is preferably used with the inventive vacuum vaporizer when the samples to be vaporized are hard-to-vaporize liquids.

The housing material which is used to form the vacuum chamber 28 can be any suitable material. The material used to form plunger 27A and case 32 which houses solenoid coil 18 and plunger 27A (as shown in FIG. 1) should preferably be a ferromagnetic material, such as soft iron. A spacer 33 made preferably of a non-ferromagnetic material such as teflon is preferably located below plunger 27A, serving to prevent plunger 27A from being completely pulled within and retained within solenoid coil 18 by residual magnetism. A small spring can be substituted for the teflon spacer.

In the practice of the invention, the inside size of vacuum chamber 28 will generally be about 10 cu. in. when the chamber is used to form a vacuum vaporizer for use in a gas chromatographic analysis system. However, the invention is not intended to be limited to any particular size of vacuum vaporizer.

The shape of the vacuum chamber 28 is preferably cylindrical for best ease in movement of the piston and for best sealing of the chamber.

A manufactured cylinder which is suitable for making in vacuum vaporizer for gas chromatography work is, for example, a Slida-Seal piston accumulator with rated volume of 10 cu. in. (164 cc), manufactured by Greer Hydraulic, Inc.

Spring 30 located within chamber 28 as shown in FIGS. 1 and 2 upon being compressed serves (together with pressure reducing means 24) to provide the force necessary to bring piston 17 back to its closed position. Therefore, a suitable spring 30 is a spring which will accomplish this function.

A suitable solenoid coil 18A is one which will quickly draw plunger 27a within solenoid coil 18A.

A 3-way microball valve 12 is the preferred type of valve for alternately introducing sample and solvent into the vacuum chamber 28 and for closing off the chamber so that a vacuum can be achieved. This is so because such a valve permits the system to be automated and provides a good seal.

The rotary stepping means can be any stepper which is compatible with the rotation of 3-way microball valve 12. For example, a 90° stepper is used with a 90° 3-way microball valve.

Pressure-reducing means 24 maintains the vapors under reduced pressure after they leave vacuum chamber 28 so that condensation does not occur, and it also serves to draw the vapors into analyzer 22. The pressure-reducing means 24 is preferably an aspirator, although a vacuum pump would also be satisfactory.

The gas chromatographic analyzer 22 can be any suitable gas chromatographic analyzer, such as for example an Optichrom 102 Process Chromatographic Analyzer, which is manufactured by Applied Automation, Inc.

The timing mechanism can be any suitable timer, such as for example Texas Instruments programmable controller, Model 5TI.

The components of the system shown in FIG. 3 are preferably connected by small diameter tubing 15, such as for example ⅛ inch tubing. Small diameter tubing is preferred because it is sufficiently large to accommodate the small samples generally used in gas chromatographic analyses.

The components shown in FIG. 3 and their relative positions with respect to each other represent preferred components and preferred positions in the gas chromatographic system. However, the entire operation can be accomplished manually and still remain within the scope of this invention. In that event, the timing mechanism 10 and stepping means 11 would be eliminated from the system. Also, 3-way microball valve 12 would be adjusted manually to admit either sample or solvent after which it would be closed; and third valve 23 would be manually opened to allow pressure-reducing means 24 to draw the gas out of the chamber and into the analyzer. After completion of the gas chromatographic analysis, the sample would be removed from the system by pressure-reducing means 24. Third valve 23 would then be manually closed, and the cycle would be complete.

This invention is intended to cover reasonable changes and modifications which would be apparent to those skilled in the art.

What is claimed is:

1. An apparatus comprising:

a first valve having a first inlet means in communication with an outlet means only when said first valve is in a first position and a second inlet means in communication with the outlet means only when said first valve is in a second position;

a heatable sealable chamber divided into a first section and a second section by a movable piston positioned within said chamber, wherein the first section of said chamber has one inlet and one outlet, wherein the second section of said chamber is in open communication with the atmosphere, wherein the second section of said chamber contains a spring exerting a force against the piston in the direction of the first section of the chamber when the spring is compressed, wherein an actuator means external to said chamber is attached to said piston which, upon actuation, quickly forces said piston in the direction of the second section of the chamber;

a second valve having an inlet means and an outlet means and which passes a fluid only from the inlet means to the outlet means;

a gas chromatographic analyzer having an inlet means and an outlet means;

a third valve having an inlet means and an outlet means and an open position and a closed position; and a pressure reducing means;

wherein the outlet means of the first valve is connected to the inlet means of the first section of the chamber;

wherein the inlet means of the second valve is connected to the outlet means of the first section of the chamber;

wherein the inlet means of the gas chromatographic analyzer is connected to the outlet means of the second valve and wherein the outlet means of the gas chromatographic analyzer is connected to the inlet means of the third valve; and wherein the pressure reducing means is connected to the outlet means of the third valve.

2. An apparatus according to claim 1 wherein said piston is actuated by a solenoid.

3. An apparatus according to claim 1 wherein said piston is actuated by a second piston which is actuated by pneumatic pressure.

4. An apparatus according to claim 1 wherein said piston is actuated by a second piston which is actuated by hydraulic pressure.

5. An apparatus according to claim 1 wherein said first valve is a 3-way microball valve.

6. An apparatus according to claim 5 wherein said first valve is operated by a rotary stepping means.

7. An apparatus according to claim 1 wherein said rotary stepping means, said piston, and said third valve are actuated by a timer.

8. An apparatus according to claim 1 wherein said pressure-reducing means is an aspirator.

* * * * *